United States Patent
Oota et al.

(10) Patent No.: US 9,724,053 B2
(45) Date of Patent: *Aug. 8, 2017

(54) X-RAY CT APPARATUS

(71) Applicant: TOSHIBA MEDICAL SYSTEMS CORPORATION, Otawara-shi (JP)

(72) Inventors: Satoshi Oota, Nikko (JP); Sakae Kimishima, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/868,009

(22) Filed: Sep. 28, 2015

(65) Prior Publication Data

US 2016/0015335 A1    Jan. 21, 2016

Related U.S. Application Data

(60) Division of application No. 13/494,559, filed on Jun. 12, 2012, now Pat. No. 9,173,619, which is a (Continued)

(30) Foreign Application Priority Data

Jan. 7, 2011    (JP) ................. 2011-001947

(51) Int. Cl.
*A61B 6/00*    (2006.01)
*A61B 6/06*    (2006.01)
(Continued)

(52) U.S. Cl.
CPC ............... *A61B 6/06* (2013.01); *A61B 6/032* (2013.01); *A61B 6/4078* (2013.01); *A61B 6/547* (2013.01);
(Continued)

(58) Field of Classification Search
CPC ............ A61B 6/032; A61B 6/06; A61B 6/547
See application file for complete search history.

(56) References Cited

U.S. PATENT DOCUMENTS 3,920,999 A    11/1975    Drexler et al.
6,215,848 B1    4/2001    Linders et al.
(Continued)

FOREIGN PATENT DOCUMENTS

CN        1419891 A    5/2003
CN     101098660 A    1/2008
(Continued)

OTHER PUBLICATIONS

Extended Search Report issued Apr. 4, 2016 in European Patent Application No. 11847882.5.
(Continued)

*Primary Examiner* — Dani Fox
(74) *Attorney, Agent, or Firm* — Oblon, McClelland, Maier & Neustadt, L.L.P.

(57) ABSTRACT

There is provided an X-ray CT apparatus including: an X-ray source; a wedge which is disposed between the X-ray source and a subject and in which a shield blocking apart of an X ray is formed; a wedge driving unit for moving position of the wedge; and a system control unit controlling the wedge driving unit during a scan execution period to control the position of the wedge.

11 Claims, 6 Drawing Sheets

Related U.S. Application Data continuation of application No. PCT/JP2011/006890, filed on Dec. 9, 2011.

(51) Int. Cl.
  *G21K 1/02* (2006.01)
  *A61B 6/03* (2006.01)
  *G21K 1/10* (2006.01)
  *A61B 6/02* (2006.01)
  *A61B 6/10* (2006.01)

(52) U.S. Cl.
  CPC .............. *G21K 1/02* (2013.01); *G21K 1/10* (2013.01); *A61B 6/027* (2013.01); *A61B 6/107* (2013.01); *A61B 6/542* (2013.01)

(56) References Cited

U.S. PATENT DOCUMENTS

| | | | |
|---|---|---|---|
| 6,233,303 B1 | 5/2001 | Tam | |
| 6,307,918 B1* | 10/2001 | Toth | A61B 6/032 378/156 |
| 6,614,877 B2 | 9/2003 | Anderton | |
| 7,170,975 B2 | 1/2007 | Distler et al. | |
| 7,515,689 B2 | 4/2009 | Baba et al. | |
| 7,706,500 B2 | 4/2010 | Kondo | |
| 2002/0037067 A1 | 3/2002 | Horiuchi | |
| 2003/0095627 A1 | 5/2003 | Anderton | |
| 2005/0053188 A1 | 3/2005 | Gohno | |
| 2006/0159221 A1 | 7/2006 | Popescu | |
| 2008/0043900 A1 | 2/2008 | Baba et al. | |
| 2010/0054395 A1* | 3/2010 | Noshi | A61B 6/032 378/16 |
| 2010/0119033 A1 | 5/2010 | Li et al. | |
| 2010/0166138 A1* | 7/2010 | Yan | A61B 6/032 378/4 |

FOREIGN PATENT DOCUMENTS

| | | |
|---|---|---|
| EP | 0 981 999 A2 | 3/2000 |
| EP | 1 192 901 A1 | 4/2002 |
| JP | 62-47346 A | 3/1987 |
| JP | 62-98300 A | 5/1987 |
| JP | 6-22951 | 2/1994 |
| JP | 7-255712 A | 10/1995 |
| JP | 2000-107163 | 4/2000 |
| JP | 2001-145621 A | 5/2001 |
| JP | 2003-38478 A | 2/2003 |
| JP | 2003-180667 A | 7/2003 |
| JP | 2005-080919 A | 3/2005 |
| JP | 2006-75339 A | 3/2006 |
| JP | 2006-175230 A | 7/2006 |
| JP | 2009-22412 A | 2/2009 |

OTHER PUBLICATIONS

Office Action issued Mar. 1, 2016 in Japanese Patent Application No. 2011-270048.
International Search Report issued Mar. 19, 2012 in PCT/JP2011/006890 filed Dec. 9, 2011.
International Written Opinion issued Mar. 6, 2012 in PCT/JP2011/006890 filed Dec. 9, 2011.
English translation of the International Preliminary Report on Patentability and Written Opinion of the International Searching Authority issued Jul. 18, 2013, in PCT/JP2011/006890.
Combined Chinese Office Action and Search Report issued Dec. 31, 2014 in Patent Application No. 201180004847.1 (with English Translation of Category of Cited Documents).
Office Action issued Jul. 7, 2015 in Japanese Patent Application No. 2011-270048 (with partial English translation).

* cited by examiner

US 9,724,053 B2

X-RAY CT APPARATUS

CROSS-REFERENCE TO RELATED APPLICATION

This application is a divisional application of U.S. application Ser. No. 13/494,559, filed Jun. 12, 2012, which is a continuation of International Application No. PCT/JP2011/006890, filed on Dec. 9, 2011, which is based upon and claims the benefit of priority from the prior Japanese Patent application No. 2011-001947, filed on Jan. 7, 2011. The entire contents of the above-identified applications are incorporated herein by reference.

FIELD

An embodiment of the present invention relates to an X-ray CT apparatus.

BACKGROUND

In a gantry of an existing X-ray CT (Computed Tomography) apparatus, a collimator is provided for a front face of an X-ray tube field. The collimator has a wedge for adjusting cutting of a soft ray and the intensity distribution of an X ray, and a slit mechanism which opens/closes in accordance with slice thickness at the time of a scan. The collimator forms a fan beam whose radiation dose is optimized, and irradiates a subject with an X ray.

In the case where the slit mechanism has a biaxial opening/closing mechanism in which right and left slits operate singularly, to suppress unnecessary irradiation of X rays generated before and after a scan, active collimation operation of controlling the width and position of an opening by varying the timings of opening the right and left slits to optimize the radiation dose can be performed. To execute the active collimation to reduce the dose of radiation to the subject, generally, a slit mechanism in an optical system has to have a biaxial opening/closing mechanism which can open/close two slits singularly. However, since the system is much more expensive than a normal optical system having no biaxial opening/closing mechanism in which two slits open/close, it is demanded to realize the active collimation operation by an inexpensive slit mechanism in which slits are opened/closed simultaneously.

According to one embodiment, an inexpensive high-performance X-ray CT apparatus with reduced radiation dose is provided.

DETAILED DESCRIPTION

According to one embodiment, an X-ray CT apparatus of an embodiment includes: an X-ray source; a wedge which is disposed between the X-ray source and a subject and in which a shield blocking a part of an X ray is formed; a wedge driving unit for moving position of the wedge; and a system control unit controlling the wedge driving unit during a scan execution period to control the position of the wedge.

Hereinafter, embodiments will be described in detail below with reference to the drawings of FIGS. 1 to 8. There are various types of X-ray CT apparatuses such as a type in which an X-ray tube and an X-ray detector are disposed opposite to each other and revolve together around a subject and a type in which a number of detection elements are arrayed in a ring shape and only an X-ray source revolves about a subject. Embodiments are applicable to any of the types. In the embodiments, a type in which an X-ray tube and an X-ray detector revolve together will be explained.

First Embodiment

Figure 1:
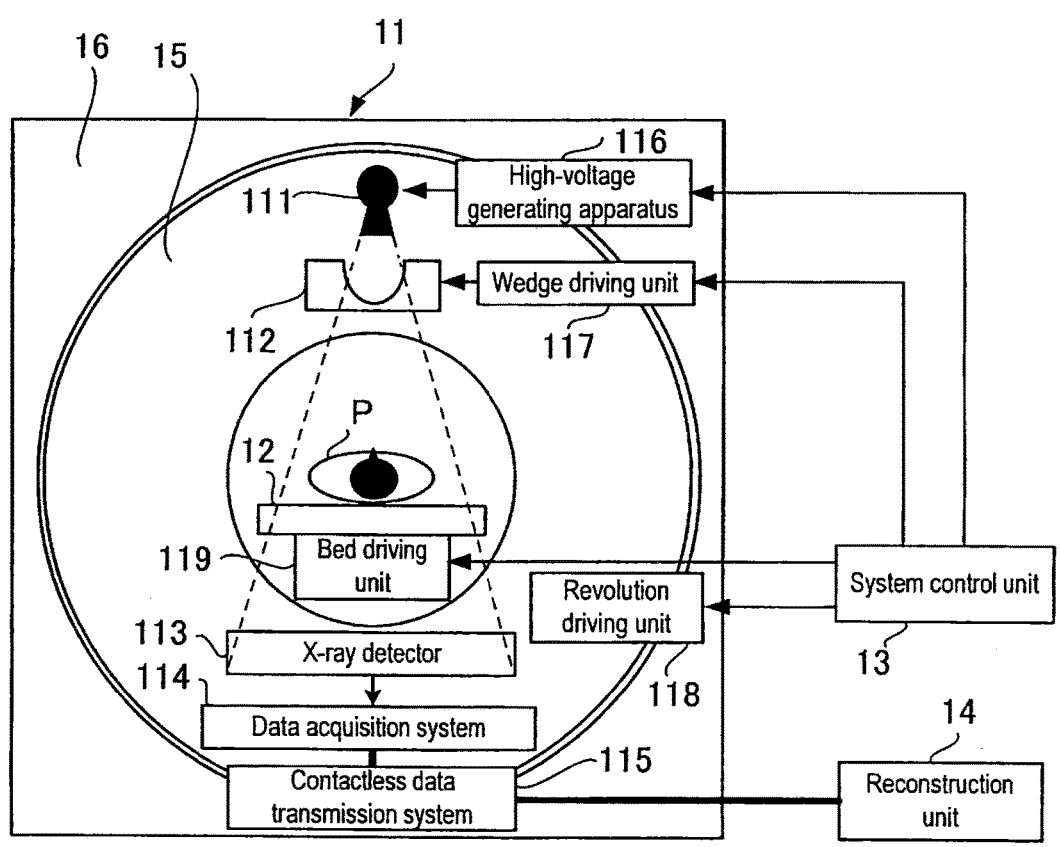
FIG. 1 is a block configuration diagram of an X-ray CT apparatus in a first embodiment.

FIG. 1 shows an X-ray CT apparatus in a first embodiment. The X-ray CT apparatus of the embodiment has a gantry 11 for scanning a subject P (patient) with an X ray, a bed 12 by which the subject P is moved into the gantry 11, a system control unit 13 for controlling the entire X-ray CT apparatus, and a reconstruction unit 14 as a computer for processing projection data obtained from the gantry 11 and reconstructing an image for medical use.

The bed 11 is constructed by a revolving part 15 which revolves around the subject P (patient) as a center and a stationary part 16 as the other part. The revolving part 15 has an X-ray tube 111 which generates an X ray, a wedge 112 for adjusting a distribution of dose of the X ray generated from the X-ray tube 111 to a fan angle direction, an X-ray detector 113 for detecting the X ray which passed through the subject P (patient), a data acquisition system (DAS) 114 for converting the data detected by the X-ray detector 113 to digital data and acquiring the digital data, and a contactless data transmission system 115 for contactlessly transmitting the projection data acquired by the data acquisition system 114 to the reconstruction unit 14 on the outside of the revolving part 15.

The system control unit 13 has a high-voltage generating apparatus 116 for generating voltage to be applied to the X-ray tube 111 for generating an X ray, a wedge driving unit 117 for moving the position of the wedge in accordance with a scanning parameter, a revolution driving unit 118 for making the revolving part 15 revolve on the basis of a scanning parameter of a helical scan or the like, and a bed driving unit 119 for moving the bed 12 on which the subject P lies into the gantry 11.

The reconstruction unit 14 reconstructs an image for medical use which is necessary for diagnosis from the projection data transferred from the contactless data transmission system 115. The reconstructed image for medical use is displayed on a not-shown monitor or the like connected to the reconstruction unit 14. The system control unit 13 and the reconstruction unit 14 are constructed generally based on a computer having high processing capability.

Figure 2A:
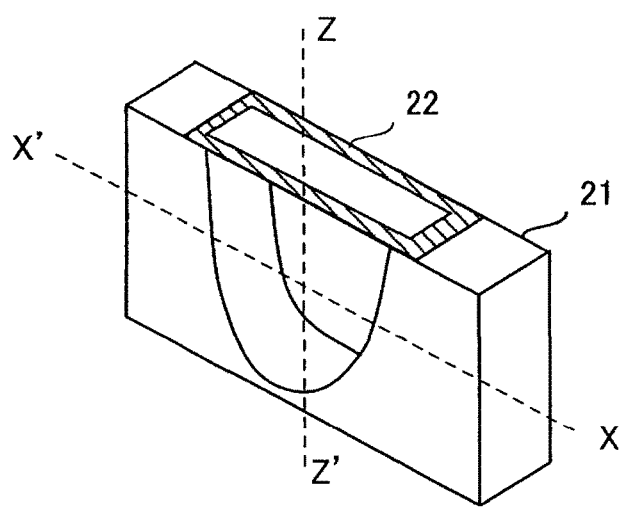
FIGS. 2A and 2B are configuration diagrams of a wedge in the X-ray CT apparatus in the embodiment.
Figure 2B:
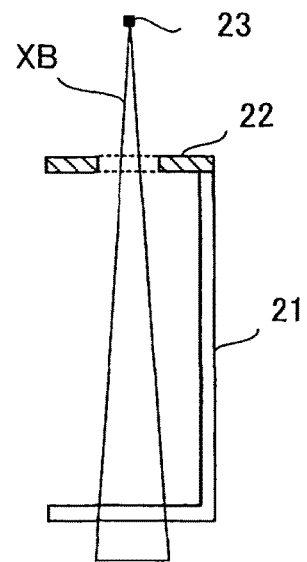

FIGS. 2A and 2B are configuration diagrams of the wedge in the X-ray CT apparatus in the embodiment. FIG. 2A is a perspective view, and FIG. 2B is a cross sectional view taken along the Z-Z' axis shown by a dotted line, and seen along line X-X'. XB indicates spread of an X-ray beam.

The wedge adjusts the X-ray dose distribution in the fan angle direction and has a U-shaped opening in its center. A plurality of kinds of wedges having different opening shapes are used in accordance with the case of scanning the subject P from the front, the case of scanning the subject P from the side, and the like, and are selected according to the scan parameters.

Since the energy of a soft X-ray is low, in reality, even when a soft X-ray is emitted from the X-ray tube 111, it is often absorbed by the subject P and does not reach the detector 113. The wedge 112 therefore also has the effect of cutting soft rays. Usually, metal such as aluminum is used for the wedge 112.

As shown in FIG. 2A, the wedge of the embodiment is obtained by adding an X-ray shield 22 to an upper part (on the X-ray tube 111 side) of a normal wedge 21. FIG. 2B shows the X-ray beam XB generated from an X-ray focal point 23 and, in the case where the X-ray focal point 23 exists around the center of the wedge 21, the X-ray shield 22 has to have, for example, a slit shape as shown in FIG. 2A by which the X ray is not blocked. In the case where the X-ray focal point 23 is deviated from the center of the wedge 21, as shown in FIG. 2B, the X-ray shield 22 has a shape like a canopy for the side face of the wedge 21. The thickness of the X-ray shield 22 is set so that most of the X ray is absorbed and is not passed. Usually, a metal which blocks an X ray such as lead can be used for the X-ray shield 22.

Figure 3:
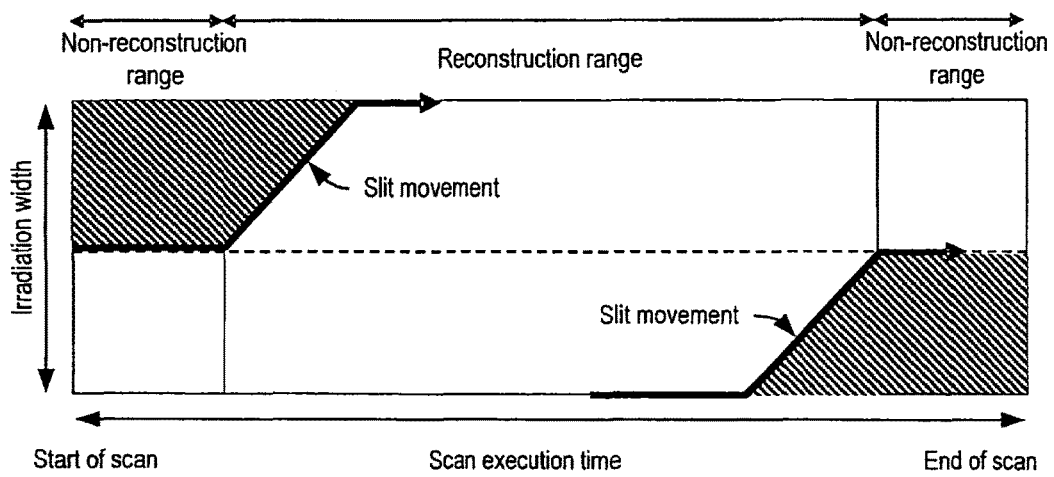
FIG. 3 is an explanation diagram of active collimation.

Referring now to FIG. 3, active collimation will be described. The horizontal axis of FIG. 3 indicates time of executing one scan, and the vertical axis indicates width of irradiation in the slice thickness direction (the body axis direction of the subject P). That is, the diagram shows how the width of irradiation to the subject P changes during execution of one scan. The irradiation width is almost proportional to the opening width of the not-shown slit mechanism.

To perform a helical scan, until an X ray is actually emitted to start a scan, acceleration time for making the speed of the revolving part 15 of the gantry constant, time for deceleration since the end of the scan until stop, running time until the moving speed of the bed 12 becomes constant, and the like are necessary. However, the times are not included in FIG. 3. "Start of scan" in FIG. 3 indicates the head of irradiation of an X ray and acquisition of data necessary for reconstruction, and "end of scan" indicates end of the data acquisition and end of irradiation of the X ray.

To reconstruct an image for medical use by a helical scan, an X ray has to be applied wider than an actual reconstruction region. Therefore, before and after the scan execution time, Excess X-ray irradiation ranges are necessary in addition to a reconstruction range. The additional X-ray irradiation ranges are defined as "non-reconstruction ranges" as ranges unnecessary for reconstruction.

In the non-reconstruction ranges before and after the scan, if the slit opening width is the same as that in the reconstruction range, due to the spread of the X-ray beam XB, a region part unnecessary for reconstruction in the subject P is also irradiated, and radiation dose is not optimized. Consequently, in a slit mechanism in which two slits can open/close singularly, in the non-reconstruction range at the start of a scan, by moving one of the slits to reduce the slit opening width which is determined according to the slice thickness to half, the width of irradiation to the subject P is reduced to half. At a time point after the non-reconstruction range, the slit opening width determined according to the slice thickness is set. In the non-reconstruction range at the end of the scan, the slit opposite to the scan start position is driven to reduce the width of irradiation to the subject P to half. By such active collimation operation, the excess X-ray irradiation before and after the scan, is suppressed and the X-ray radiation dose is optimized.

In the embodiment, by using the wedge shown in FIGS. 2A and 2B, the active collimation operation for reducing X-ray radiation dose can be performed also by the slit mechanism having no biaxial opening/closing mechanism in which two slits can open/close singularly. Therefore, it is assumed that an X ray is applied to the subject P with the same slit opening width during scan execution.

Figure 4:
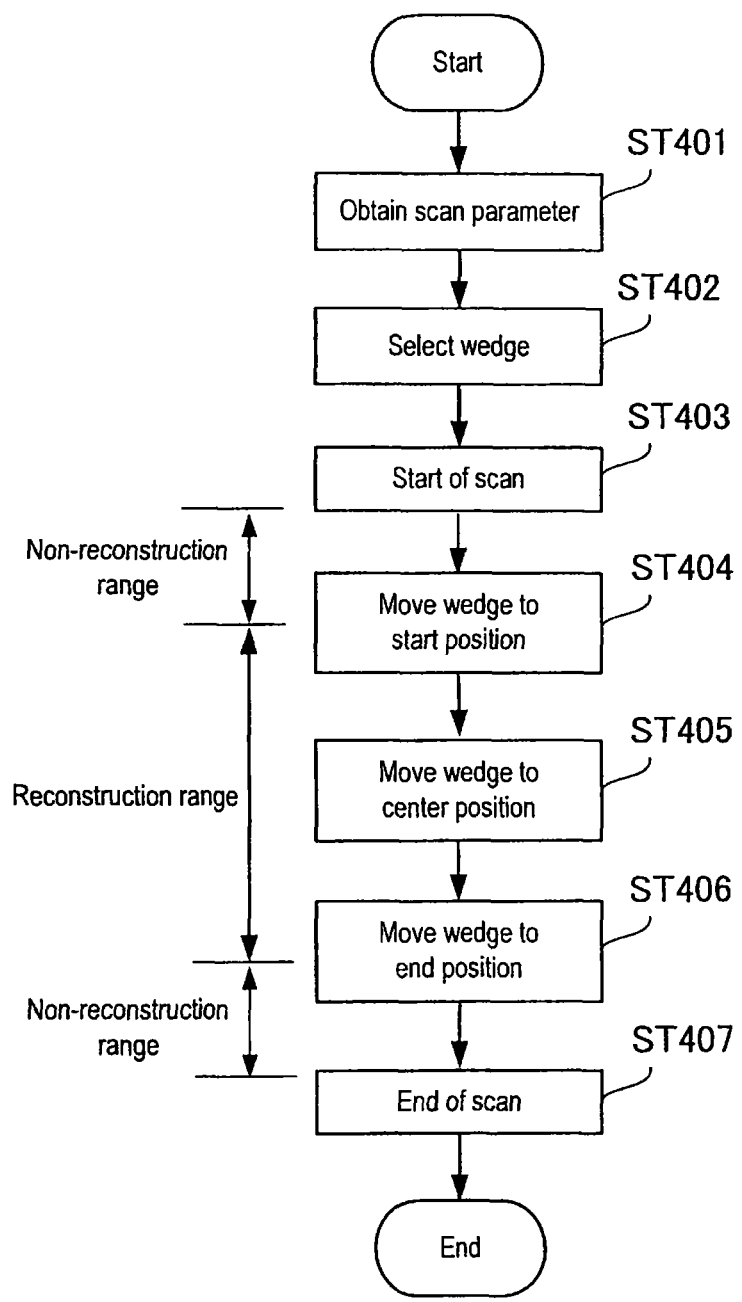
FIG. 4 is a flowchart diagram of active collimation operation in the embodiment.
Figure 5A:
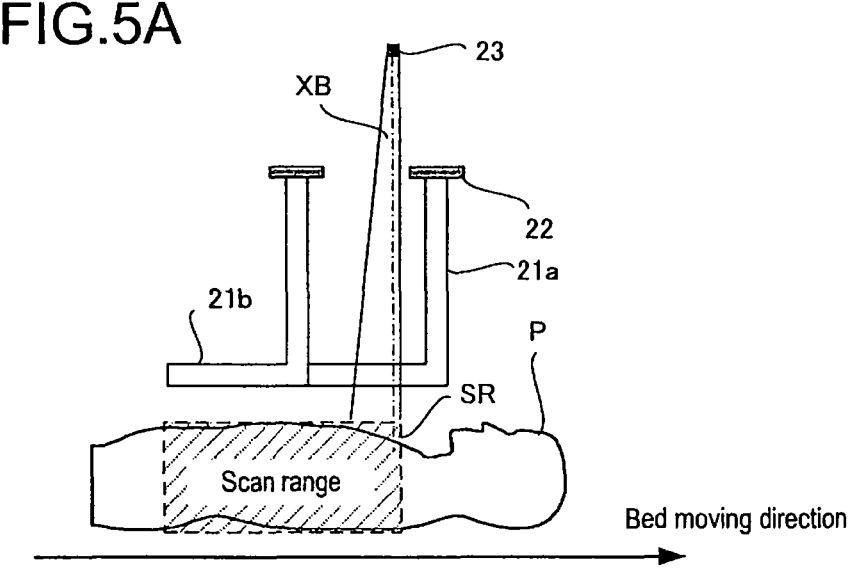
FIGS. 5A to 5C are explanatory diagrams of the active collimation operation by a wedge in the embodiment.
Figure 5B:
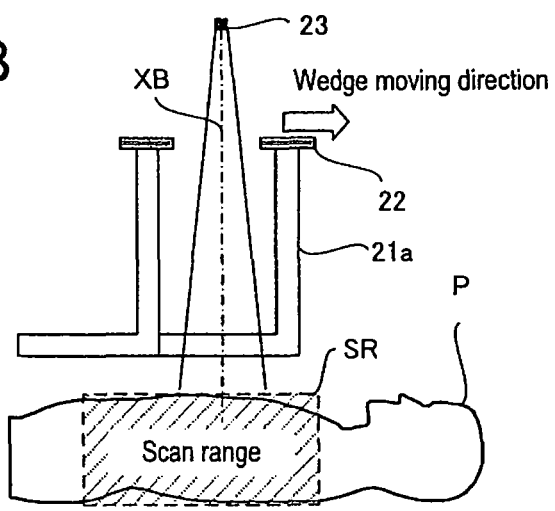
Figure 5C:
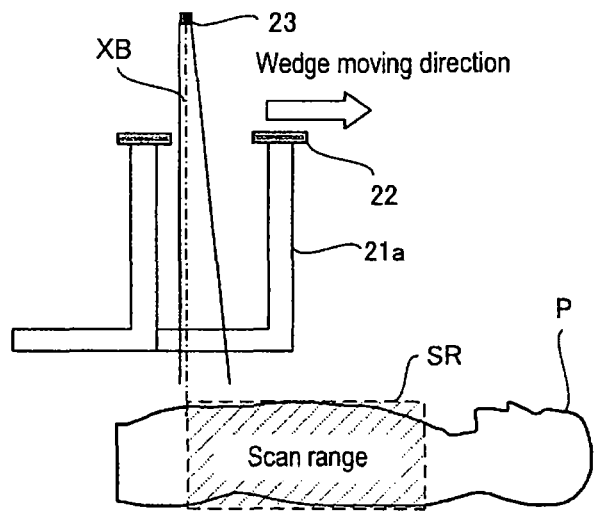

FIG. 4 is a flowchart diagram of active collimation operation in the embodiment. FIGS. 5A to 5C are diagrams for explaining the active collimation operation using the wedge in the embodiment. FIG. 5A is an explanatory diagram at the start of a scan (non-reconstruction range), FIG. 5B is an explanatory diagram during the scan (reconstruction range), and FIG. 5C is an explanatory diagram at the end of the scan (non-reconstruction range). XB indicates the spread of the X-ray beam like in FIG. 2, and a square SR shown by the dotted lines shows a scan range.

First, a doctor or laboratory technician makes the subject P lie on the bed 12 and enters a scan parameter for an image for medical use to be acquired from the subject P. In step ST401, the system control unit 13 obtains the entered scan parameter and executes a scan on the basis of the scan parameter.

A plurality of wedges 21 (112) are mounted in the gantry 11. In step ST402, a wedge adapted to the scan parameter, the build of the subject P, the image acquisition direction, and the like is selected. In FIG. 5A, wedges 21a and 21b are shown, and the wedge 21a is selected.

In step ST403, execution of a scan is started on the basis of a scan schedule of the non-reconstruction range and the reconstruction range calculated by the scan parameter.

In step ST404, at the time point when the revolving speed of the revolving part 15 of the gantry and the moving speed of the bed 12 become constant, the slit of the not-shown slit mechanism is opened to apply an X ray, and the scan is started. As shown in FIG. 5A, in the non-reconstruction range at the start of the scan, the system control unit 13 controls the wedge driving unit 117 to move the wedge 21a to a position where the X ray is not applied on the outside of the scan range SR, thereby suppressing spread of the X-ray beam XB. Consequently, the dose of irradiation of the X ray to the subject P in the non-reconstruction range is reduced to half.

In step ST405, in the reconstruction range after the non-reconstruction range at the start of the scan, the system control unit 13 further controls the wedge driving unit 117 to move the wedge 21a in the direction of the outline arrow shown in FIG. 5B, thereby controlling the focal point 23 of the X ray to be positioned in the center of the wedge 21a. At this time point, the X-ray beam XB is not interrupted by the X-ray shield 22.

In step ST406, as shown in FIG. 5C, in the non-reconstruction range at the end of the scan, the wedge 21a is further moved by the wedge driving unit 117 to a position where the X ray is not applied on the outside of the scan range SR, thereby suppressing spread of the X-ray beam XB. Consequently, the dose of the X ray to the subject P in the non-reconstruction range is reduced to half. In step ST407, the scan is finished.

By moving the position of the wedge 21a during the scan execution, without the slit mechanism in which two slits can open/close singularly, the active collimation operation can be performed.

As described above, in the first embodiment, also in the low-price X-ray CT apparatus having the slit mechanism which performs only the simultaneous opening operation, if the apparatus has the wedge driving unit, the active collimation can be performed by using the wedge of the embodiment. Since the active collimation operation is enabled only by changing firmware or software of the wedge driving unit, it greatly contributes to lower price and higher performance of the apparatus.

Second Embodiment

Figure 6A:
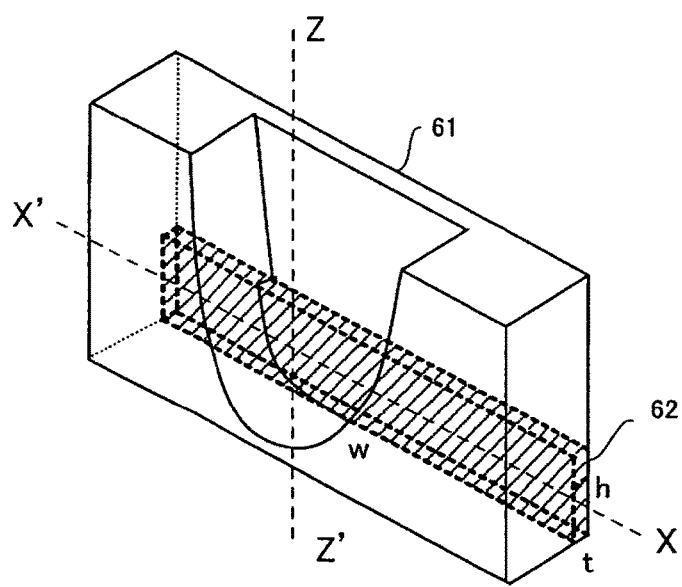
FIGS. 6A and 6B are configuration diagrams of a wedge in an X-ray CT apparatus in a second embodiment.
Figure 6B:
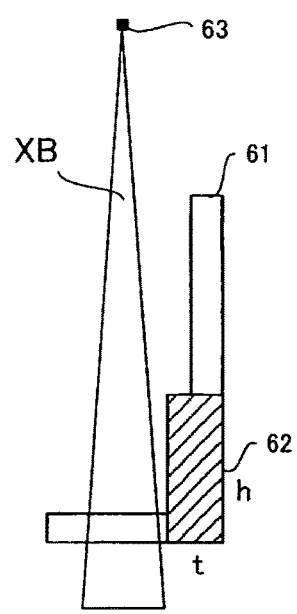

FIGS. 6A and 6B show a modification of the wedge. FIG. 6A is a perspective view, and FIG. 6B is a cross sectional view taken along the Z-Z' axis shown by a dotted line, and seen along line X-X'.

In the first embodiment, the X-ray shield 22 is disposed in the upper part (on the X-ray tube 111 side) of the wedge 21. In the second embodiment, an X-ray shield 62 is disposed in a side face of a wedge 61.

In the case of disposing the X-ray shield 62 in the side face of the wedge 61, thickness "t" and height "h" of the X-ray shield 62 are determined in consideration of the spread of the X-ray beam. Width "w" is set to almost the same as the width of the wedge 61. In the first embodiment, to prevent the opening shape of the wedge 21 from changing, the X-ray shield 22 is additionally disposed on the X-ray tube 111 side of the wedge 21. Due to this, there is the possibility that mechanical dimensions of the wedge change. However, in the embodiment, the X-ray shield 62 can be embedded in the side face of the wedge 61, so that the wedge can be designed in the same dimensions as those of the original wedge. Consequently, there is no mechanical restriction such that attachment to the conventional X-ray CT apparatus is impossible.

As described above, in the second embodiment, in addition to the effect of the first embodiment, the mechanical restriction can be eliminated and an effect that the wedge of the embodiment can be attached to any conventional X-ray CT apparatus is produced.

Third Embodiment

There is a specification type of an X-ray CT apparatus in which, at the time of driving a wedge, position information is reset once to assure the position precision of the wedge, and the wedge position is reset to the original position. In the X-ray CT apparatus having such a specification, the active collimation operation of the embodiment cannot be realized in a scan cycle time. Consequently, by adding a novel position detecting method to the operation of movement between the position where an X ray is blocked in the non-reconstruction range and the wedge center position in the reconstruction range, the operation can be realized.

The wedge driving unit 117 of the X-ray CT apparatus of the embodiment will be described with reference to FIG. 7.

Figure 7:
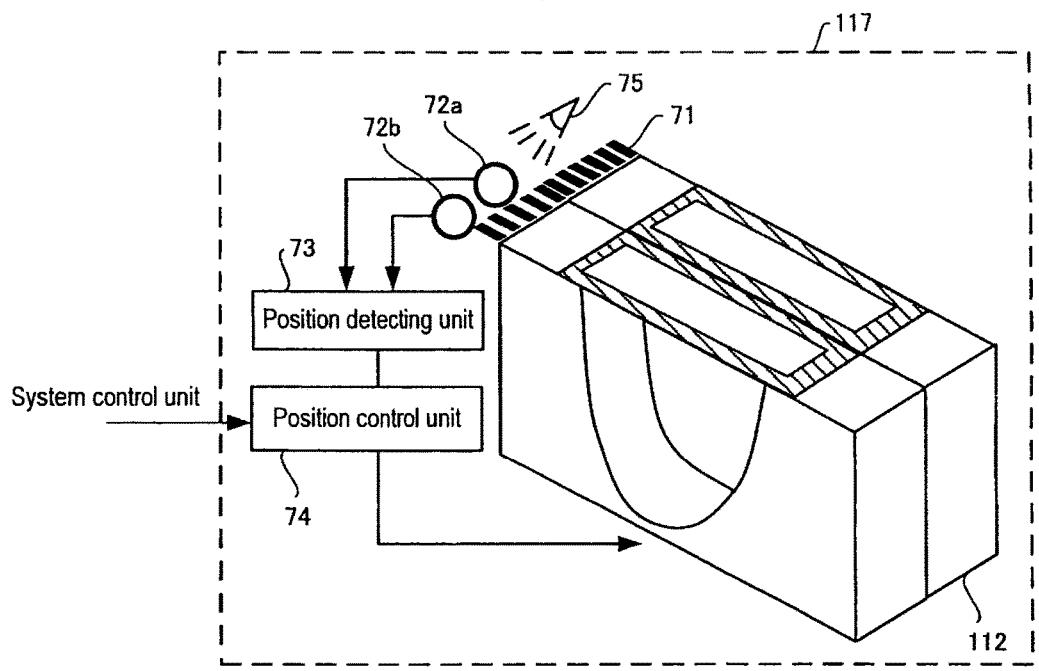
FIG. 7 is a block configuration diagram of a wedge driving unit in a third embodiment.

As shown in FIG. 7, the wedge driving unit 117 has a ladder pattern 71 disposed for position detection on the top or side face of the wedge 112, a position detecting unit 73 for detecting the position of the wedge 112 from photosensors 72a and 72b which read the positional relation of the ladder pattern 71 disposed on the wedge 112 in accordance with a reflection ratio of light, a position control unit 74 for controlling the wedge 112 between a position where an X ray is blocked and a wedge center position on the basis of an output of the position detecting unit 73, and a motor for driving the wedge to a predetermined position in response to a control signal from the position control unit. As necessary, an illumination light 75 which illuminates the ladder pattern 71 is added.

For example, the ladder pattern 71 is a pattern of black and white. In the position where the wedge 112 blocks the X ray, the photosensor 72a receives reflection light (reflects by the white pattern), and the photosensor 72b does not receive reflection light (absorbs by the black pattern). When the wedge 112 is in the wedge center position, the photosensor 72a does not receive reflection light, and the photosensor 72b has the pattern of receiving reflection light. The photosensors 72a and 72b are disposed to face the ladder pattern 71 so that the position relation can be discriminated. In the case where there is a plurality of wedges, the wedges may have different ladder patterns.

Therefore, the photosensor 72a constructed as described above will be called a center position sensor 72a, and the photosensor 72b will be called a block position sensor 72b.

Figure 8:
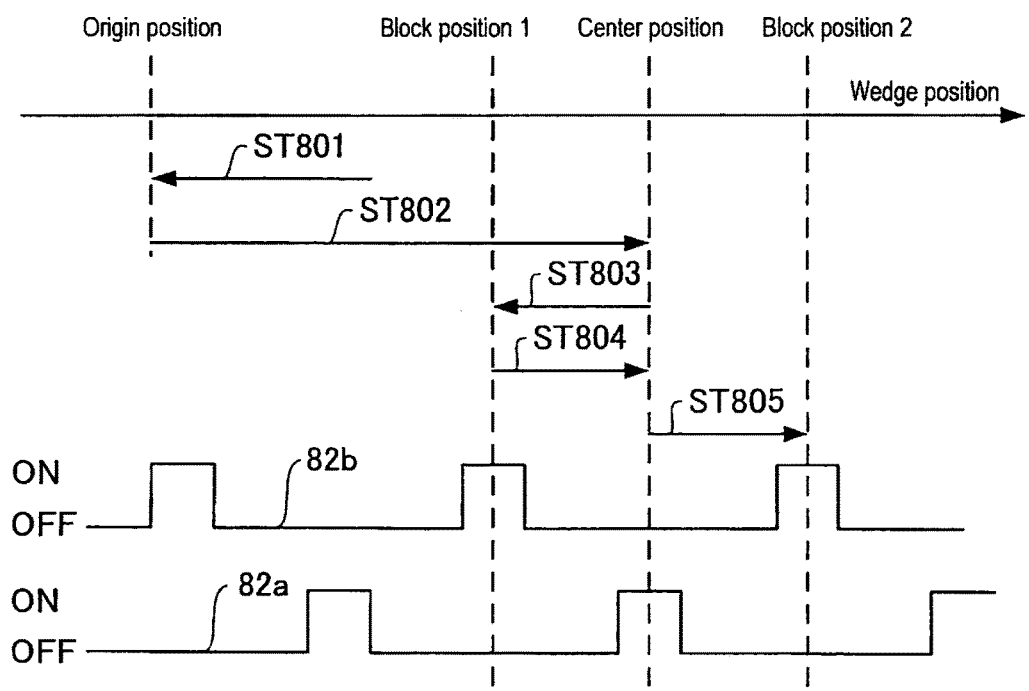
FIG. 8 is a time chart diagram of active collimation operation in the embodiment.

FIG. 8 shows a time chart of the active collimation operation in the embodiment. It illustrates an output waveform 82a of the center position sensor 72a, and an output waveform 82b of the block position sensor 72b. Using FIG. 8, control on the wedge 112 since the start of a scan to the end of the scan will be described.

To select a predetermined wedge from the plurality of wedges 112, in an arrow indicated by step ST801, the position control unit 74 controls the motor to reset the wedge to the origin position. In step ST802, the position control unit 74 performs the position control to the center position of the selected wedge 112.

In the non-reconstruction range at the scan start, like the arrow shown by step ST803, the motor is reversely rotated to perform the position control to block position 1, and a scan is started. In the block position 1, the output waveform 82b of the block position sensor 72b becomes "ON", and the output waveform 82a of the center position sensor 72a becomes "OFF". In such a manner, the control can be performed.

In the reconstruction range, like the arrow shown by the step ST804, the motor is forwardly rotated to perform control to the center position. In the center position, the output waveform 82a of the center position sensor 72a becomes "ON" from "OFF", and the output waveform 82b of the block position sensor 72b becomes "OFF" from "ON". In such a manner, the control can be performed.

Further, in the non-reconstruction range close to the scan end, like the arrow shown by the step ST805, the motor is forwardly rotated to perform control to the block position 2. In the block position 2, the output waveform 82b of the block position sensor 72b becomes "ON" from "OFF", and the output waveform 82a of the center position sensor 72a becomes "OFF" from "ON". In such a manner, the control can be performed.

As described above, in the third embodiment, also in the X-ray CT apparatus having the specification of resetting the wedge position to the origin position at the time of driving the wedge, the active collimation operation can be performed. Moreover, the attached ladder pattern 71, the photosensors 72, and the like are inexpensive and they are small and do not take up much space, so that there is hardly mechanical restriction. Consequently, an effect that the wedge of the embodiment can be attached to any conventional X-ray CT apparatus is produced.

In the case where there is room in the X-ray CT apparatus, an encoder or the like may be attached in place of the ladder pattern 71 and the photosensors 72, and the motor may be controlled by an output of the encoder to realize the active collimation operation.

The present invention is not limited to the foregoing embodiments and can be variously modified. For example, the shape of the X-ray shield added to the wedge shown in the embodiments is merely an example, and various shapes can be employed.

Although the X-ray CT apparatus having the revolving part is especially described in the foregoing embodiments, for example, also in an X-ray apparatus having no revolving part, an X-ray beam can be blocked partially or entirely by moving a wedge to which an X-ray shield is added.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and sprit of the inventions.

What is claimed is:

1. An X-ray CT apparatus, comprising:
a wedge configured to adjust a distribution of dose of an X ray emitted from an X-ray source;
a shield added to the wedge;
a wedge driving unit moving the wedge in a slice thickness direction; and
a system control unit controlling the wedge driving unit to move the wedge during a scan execution period,
wherein the system control unit controls the wedge driving unit to move the wedge to a first position where an X ray, spreading in the slice thickness direction of the X-ray source and unnecessary for reconstruction of an image for medical use, is blocked by the shield in a non-reconstruction range at the start of the scan execution period, or controls the wedge driving unit to move the wedge to a second position where the X ray unnecessary for reconstruction of the image for medical use is blocked by the shield in the non-reconstruction range at the end of the scan.

2. The X-ray CT apparatus according to claim 1,
wherein the system control unit controls the wedge driving unit to move the wedge to a third position where the X ray is not blocked by the shield in a reconstruction range of the image for medical use.

3. An X-ray CT apparatus, comprising:
a wedge configured to adjust a distribution of dose of an X ray emitted from an X-ray source;
a shield added to the wedge;
a wedge driving unit moving the wedge in a slice thickness direction; and
a system control unit controlling the wedge driving unit to move the wedge during a scan execution period,
wherein the system control unit controls the wedge driving unit to move the wedge to a first position where an X ray, spreading in the slice thickness direction of the X-ray source and unnecessary for reconstruction of an image for medical use, is blocked by the shield in a non-reconstruction range at the start of the scan execution period, controls the wedge driving unit to move the wedge in a second position where the X ray unnecessary for reconstruction of the image for medical use is blocked by the shield in the non-reconstruction range at the end of the scan, and controls the wedge driving unit to move the wedge to a third position where the X ray is not blocked by the shield in a reconstruction range of the image for medical use.

4. The X-ray CT apparatus according to claim 3,
wherein the wedge driving unit has a position detecting unit configured to detect the first and second positions where the X ray is blocked and the third position.

5. The X-ray CT apparatus according to claim 4,
wherein the position detecting unit comprises a block position sensor configured to detect the first and second positions where the X ray is blocked, and a center position sensor configured to detect the third position.

6. The X-ray CT apparatus according to claim 5,
wherein each of the block position sensor and the center position sensor is constructed by a photosensor, and a ladder pattern of different reflection ratios is disposed in the wedge so that reflection light enters the block position sensor in the first and second positions and reflection light enters the center position sensor in the third position.

7. An X-ray CT apparatus, comprising:
a wedge configured to adjust a distribution of dose of an X ray emitted from an X-ray source;
a shield added to the wedge;
a wedge driving unit moving the wedge in a slice thickness direction; and
a system control unit controlling the wedge driving unit to move the wedge during a scan execution period,
wherein the shield is added to at least one of both ends of the wedge in the slice thickness direction, and along a fan angle direction of the wedge, and
wherein the system control unit controls the wedge driving unit to move the wedge to a first position where an X ray, spreading in the slice thickness direction of the X-ray source and unnecessary for reconstruction of an image for medical use, is blocked by the shield in a non-reconstruction range at the start of the scan execution period, or controls the wedge driving unit to move the wedge to a second position where the X ray unnecessary for reconstruction of the image for medical use is blocked by the shield in the non-reconstruction range at the end of the scan.

8. The X-ray CT apparatus according to claim 7,
wherein the system control unit controls the wedge driving unit to move the wedge to a third position where the X ray is not blocked by the shield in a reconstruction range of the image for medical use.

9. An X-ray CT apparatus, comprising:
a wedge configured to adjust a distribution of dose of an X ray emitted from an X-ray source;
a shield added to the wedge;
a wedge driving unit moving the wedge in a slice thickness direction; and
a system control unit controlling the wedge driving unit to move the wedge during a scan execution period,
wherein the shield is added to at least one of both ends of the wedge in the slice thickness direction, and along a fan angle direction of the wedge, and
wherein the system control unit controls the wedge driving unit to move the wedge to a first position where an X ray, spreading in the slice thickness direction of the X-ray source and unnecessary for reconstruction of an image for medical use, is blocked by the shield in a non-reconstruction range at the start of the scan execution period, controls the wedge driving unit to move the wedge in a second position where the X ray unnecessary for reconstruction of the image for medical use is blocked by the shield in the non-reconstruction range at the end of the scan, and controls the wedge driving unit to move the wedge to a third position where the X ray is not blocked by the shield in a reconstruction range of the image for medical use.

10. The X-ray CT apparatus according to claim 9, wherein the position detection unit comprises a block position sensor configured to detect the first and second positions where the X ray is blocked, and a center position sensor configured to detect the third position.

11. The X-ray CT apparatus according to claim 10, wherein each of the block position sensor and the center position sensor is constructed by a photosensor, and a ladder pattern of different reflection ratios is disposed in the wedge so that reflection light enters the block position sensor in the first and second positions and reflection light enters the center position sensor in the third position.

* * * * *